(12) United States Patent
Cleveland et al.

(10) Patent No.: US 10,849,649 B2
(45) Date of Patent: Dec. 1, 2020

(54) HIP OBTURATOR AND METHOD FOR ATRAUMATIC HIP ACCESS

(71) Applicant: DePuy Mitek, LLC, Raynham, MA (US)

(72) Inventors: Benjamin Cleveland, North Grafton, MA (US); Bethany F. Grant, Scituate, MA (US); Jeffery Tolonen, Franklin, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 255 days.

(21) Appl. No.: 15/157,610

(22) Filed: May 18, 2016

(65) Prior Publication Data

US 2016/0256192 A1     Sep. 8, 2016

Related U.S. Application Data

(62) Division of application No. 13/480,509, filed on May 25, 2012, now Pat. No. 9,364,260.

(51) Int. Cl.

| | | |
|---|---|---|
| *A61B 17/34* | (2006.01) | |
| *A61B 1/317* | (2006.01) | |
| *A61B 17/17* | (2006.01) | |
| *A61B 17/16* | (2006.01) | |
| *A61B 17/32* | (2006.01) | |
| *A61B 17/3205* | (2006.01) | |

(Continued)

(52) U.S. Cl.
CPC ...... *A61B 17/3211* (2013.01); *A61B 17/1666* (2013.01); *A61B 17/3209* (2013.01); *A61B 1/317* (2013.01); *A61B 17/1746* (2013.01); *A61B 17/320016* (2013.01); *A61B 17/32053* (2013.01); *A61B 17/3423* (2013.01); *A61B 17/3496* (2013.01); *A61B 2017/22038* (2013.01); *A61B 2017/32113* (2013.01); *A61B 2017/3454* (2013.01)

(58) Field of Classification Search
CPC ............ A61B 17/3211; A61B 17/1666; A61B 17/3209; A61B 2017/22038; A61B 2017/32113; A61B 17/320016; A61B 17/32053; A61B 17/3423; A61B 17/3496; A61B 2017/3454
See application file for complete search history.

(56) References Cited

U.S. PATENT DOCUMENTS

| | | |
|---|---|---|
| 4,237,892 A | 12/1980 | Ritter |
| 4,580,563 A | 4/1986 | Gross |

(Continued)

FOREIGN PATENT DOCUMENTS

| | | |
|---|---|---|
| CN | 1794952 A | 6/2006 |
| JP | 2002-538933 | 11/2002 |

(Continued)

*Primary Examiner* — Laura A Bouchelle
*Assistant Examiner* — Justin L Zamory

(57) ABSTRACT

An obturator provides access to a joint through a capsule surrounding the joint. A distal end of the obturator has a first distal location with a first width dimension and a second distal location with a second width dimension, wherein the second distal location is proximal to the first distal location and the second width dimension greater than the first width dimension. A retractable blade can extend from the obturator to be exposed between the first distal location and the second distal location.

9 Claims, 16 Drawing Sheets

(51) Int. Cl.
*A61B 17/3211* (2006.01)
*A61B 17/3209* (2006.01)
*A61B 17/22* (2006.01)

(56) References Cited

U.S. PATENT DOCUMENTS

| | | |
|---|---|---|
| 4,640,296 A | 2/1987 | Schnepp-Pesch |
| 4,712,547 A | 12/1987 | Bonnet |
| 4,723,546 A | 2/1988 | Zagorski |
| 4,790,312 A | 12/1988 | Capuano, Sr. |
| 4,873,991 A | 10/1989 | Skinner |
| 4,885,004 A | 12/1989 | Pao |
| 4,903,709 A | 2/1990 | Skinner |
| 5,292,330 A | 3/1994 | Shutt |
| 5,295,980 A | 3/1994 | Ersek |
| 5,342,397 A | 8/1994 | Guido |
| 5,387,215 A | 2/1995 | Fisher |
| 5,403,344 A | 4/1995 | Allen |
| 5,449,001 A | 9/1995 | Terwilliger |
| 5,470,339 A | 11/1995 | Lerrick |
| 5,607,440 A | 3/1997 | Danks |
| 5,628,762 A | 5/1997 | Al Tameem |
| 5,690,663 A | 11/1997 | Stephens |
| 5,769,865 A | 6/1998 | Kermode |
| 5,772,676 A | 6/1998 | Cuschieri |
| 5,843,108 A | 12/1998 | Samuels |
| 5,857,995 A | 1/1999 | Thomas |
| 5,893,861 A | 4/1999 | Yumoto |
| 6,017,356 A | 1/2000 | Frederick |
| 6,048,354 A | 4/2000 | Lawrence |
| 6,139,560 A | 10/2000 | Kremer |
| 6,193,715 B1 | 2/2001 | Wrublewski et al. |
| 6,270,501 B1 | 8/2001 | Freiberg |
| 6,299,622 B1 * | 10/2001 | Snow ............... A61B 17/32075 606/159 |
| 6,346,115 B1 | 2/2002 | Lawrence |
| 6,602,267 B2 | 8/2003 | Castañeda |
| 6,716,180 B2 | 4/2004 | Fontenot |
| 7,041,107 B2 | 5/2006 | Pohjonen |
| 7,320,694 B2 | 1/2008 | O'Heeron |
| 7,341,596 B2 | 3/2008 | Heppler |
| 7,780,690 B2 | 8/2010 | Rehnke |
| 2003/0004513 A1 * | 1/2003 | Guzman ............. A61B 17/1635 606/62 |
| 2004/0167554 A1 | 8/2004 | Simpson |
| 2004/0181246 A1 | 9/2004 | Heppler |
| 2006/0184187 A1 * | 8/2006 | Surti ............... A61B 17/32002 606/170 |
| 2006/0206115 A1 * | 9/2006 | Schomer ........... A61B 10/0275 606/79 |
| 2006/0217737 A1 | 9/2006 | Iversen |
| 2007/0225740 A1 * | 9/2007 | Suddaby ........... A61B 17/3211 606/170 |
| 2008/0077146 A1 | 3/2008 | Pernsteiner |
| 2009/0157110 A1 | 6/2009 | Muto |
| 2009/0182367 A1 | 7/2009 | Hickingbotham |
| 2010/0100111 A1 | 4/2010 | Rogerson |
| 2010/0262174 A1 | 10/2010 | Sretavan |
| 2011/0087258 A1 | 4/2011 | Sluss |
| 2011/0319839 A1 | 12/2011 | Del Vecchio |
| 2012/0157999 A1 | 6/2012 | Ochiai |
| 2012/0239070 A1 | 9/2012 | Wijay |
| 2015/0011941 A1 | 1/2015 | Saeki |

FOREIGN PATENT DOCUMENTS

| | | |
|---|---|---|
| WO | WO 2008103308 A1 | 8/2008 |
| WO | WO 2012044633 A1 | 4/2012 |

\* cited by examiner

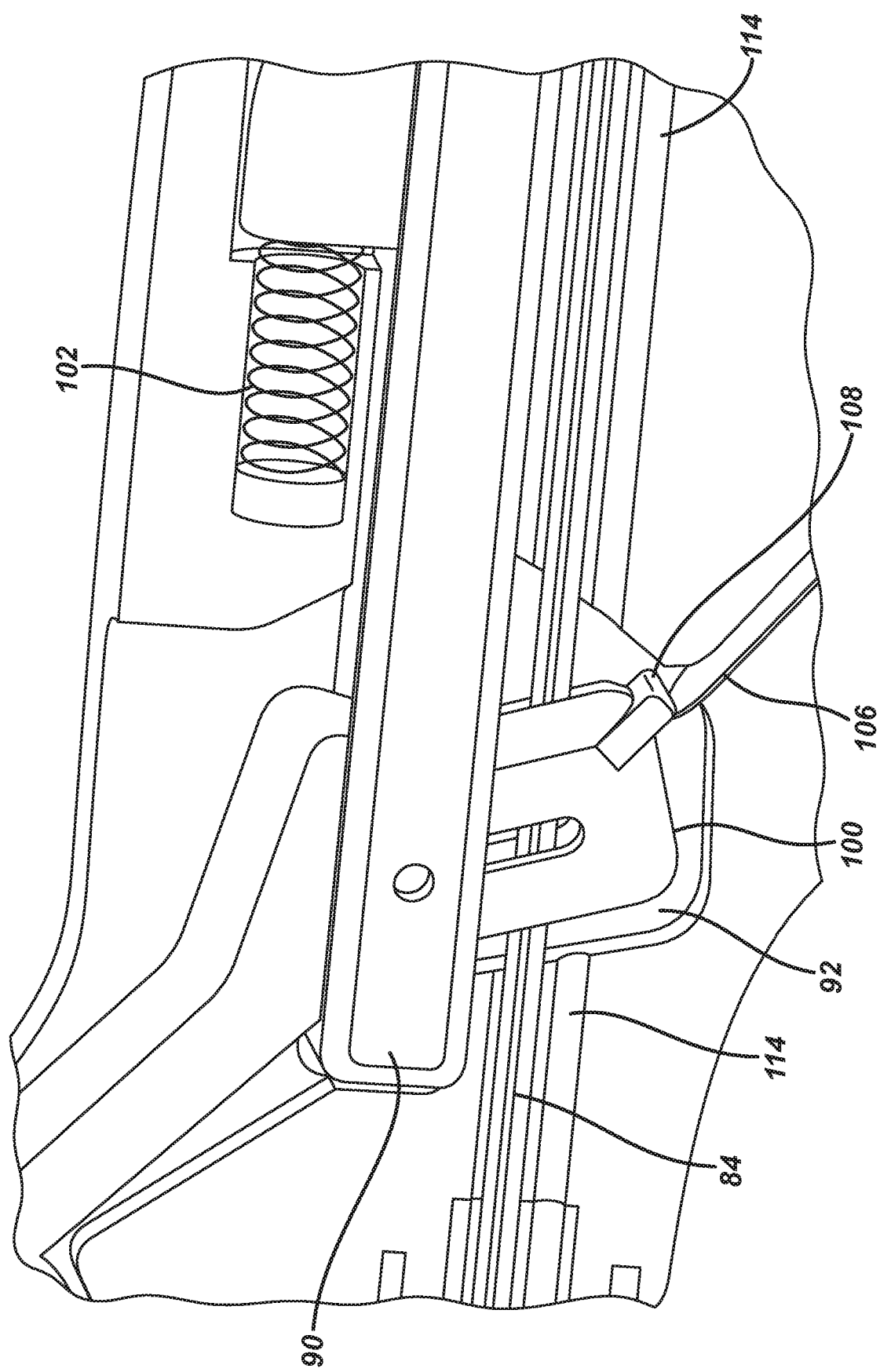

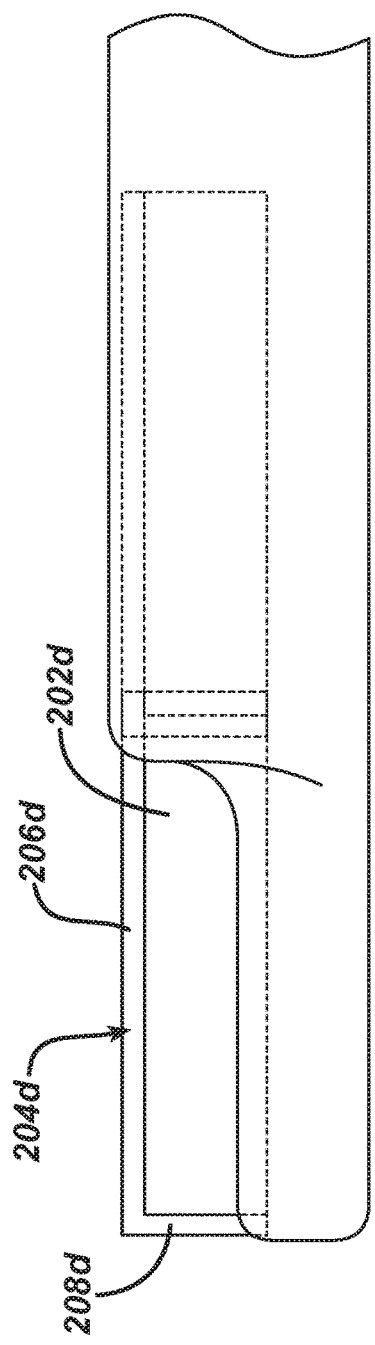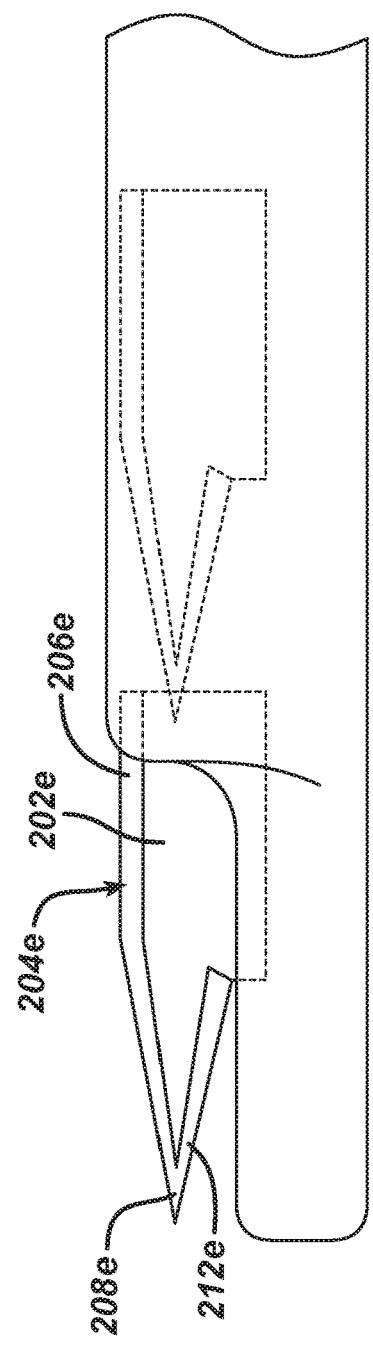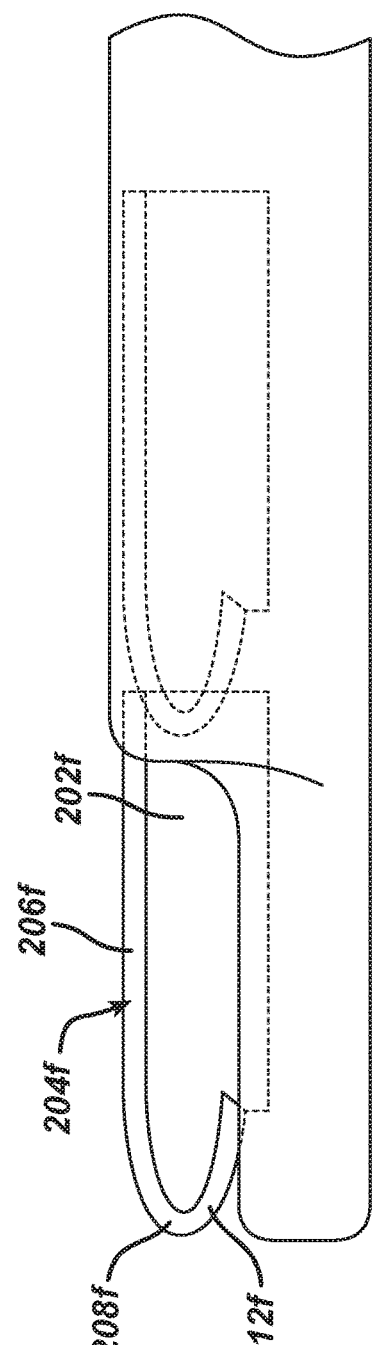

HIP OBTURATOR AND METHOD FOR ATRAUMATIC HIP ACCESS

CROSS REFERENCE TO RELATED APPLICATIONS

This application is a divisional application of U.S. patent application Ser. No. 13/480,509, entitled HIP OBTURATOR AND METHOD FOR ATRAUMATIC HIP ACCESS, filed May 25, 2012, the entire contents of which are hereby incorporated by reference.

BACKGROUND

This application relates to surgical tools and methods for providing access to a joint, in particular to a hip joint.

The hip joint is enclosed by a protective capsule that encloses the head of the femur and a large portion of the neck of the femur. To perform surgery on a hip joint a surgeon must first penetrate the capsule to gain access to the interior of the joint. Current access techniques involve introducing an extended length spinal needle and following this with a Nitinol guidewire. A cannulated dilator having a bullet nosed distal end with a final diameter of about 4.5 to 5.5 mm is passed over the guidewire and forced through the capsule. Penetration of the capsule with this instrument requires substantial force and it is not uncommon for the instrument to plunge through the capsule in an uncontrolled manner impacting and sometimes damaging the femoral head, labrum or acetabular cartilage therein.

SUMMARY OF THE INVENTION

The present invention overcomes these and other limitations of the prior art in a simple and elegant design.

A surgical instrument according to the present invention comprises a hip arthroscopy obturator for penetrating a hip capsule. The obturator comprises an axially elongated body having a distal end, a cannulation through the body to the distal end, and a retractable blade comprising a cutting edge and having a retracted position in which the cutting edge is disposed in the body and an extended position in which the cutting edge extends out of the body at the distal end.

Preferably, the blade is biased toward the retracted position. Preferably, a manually engageable actuator is positioned proximal of the body distal end and connected to the blade to allow a user to extend the blade to the extended position.

Preferably, the body has a central longitudinal axis and the cannulation is offset laterally therefrom at the distal end. Preferably, a distal tip of the body at the body distal end has an outer diameter narrower than a body distal end diameter forming a distally facing abutment therebetween. Preferably, the blade is movable from the retracted position to the extended position through the abutment. Preferably, when the blade is in the extended position the cutting edge does not extend distally beyond the distal tip nor laterally beyond the body distal end diameter. Preferably, the cannulation extends through the distal tip.

Preferably, a guide wire extends through the cannulation.

Preferably, a cannula is further provided having an axial lumen therethrough, the obturator being received within the lumen.

A method according to the present invention provides for accessing a hip capsule in a hip arthroscopy procedure. The method comprises the steps of: contacting the hip capsule with a distal end of an obturator comprising an axially elongated body; and extending a retractable blade having a cutting edge from a retracted position in which the cutting edge is disposed within the body to an extended position in which the cutting edge extends out of the body at the distal end and against the hip capsule to cut the hip capsule.

Preferably, the method further includes the steps of passing a guide wire through the hip capsule into a hip joint space and passing over the guide wire the obturator to contact the hip capsule with the distal end thereof.

Preferably, after cutting the hip capsule with the cutting edge, the blade is retracted to the retracted position. Thereafter additional cuts can be made. The obturator can be moved inward of the hip capsule through that portion thereof already cut by the cutting edge and then the blade again extended to the extended position to further cut the hip capsule. Alternatively, the obturator can be rotated and the blade then again extended to the extended position to further cut the hip capsule. A series of such further inward cuts and rotation cuts can be employed together in a procedure.

Preferably, the blade is biased toward the retracted position. After extending the blade and cutting the hip capsule the blade is released to return the blade to its retracted position.

In one aspect of the invention a cannula having an axial lumen therethrough is passed through the hip capsule where it was cut by the cutting edge.

BRIEF DESCRIPTION OF THE DRAWINGS

FIG. 7C is an enlarged perspective view in cross-section of the obturator of FIG. 7A;

FIGS. 12A to 12F are side elevation views of an obturator according to the present invention having alternative blade shapes.

DETAILED DESCRIPTION

Figure 1:
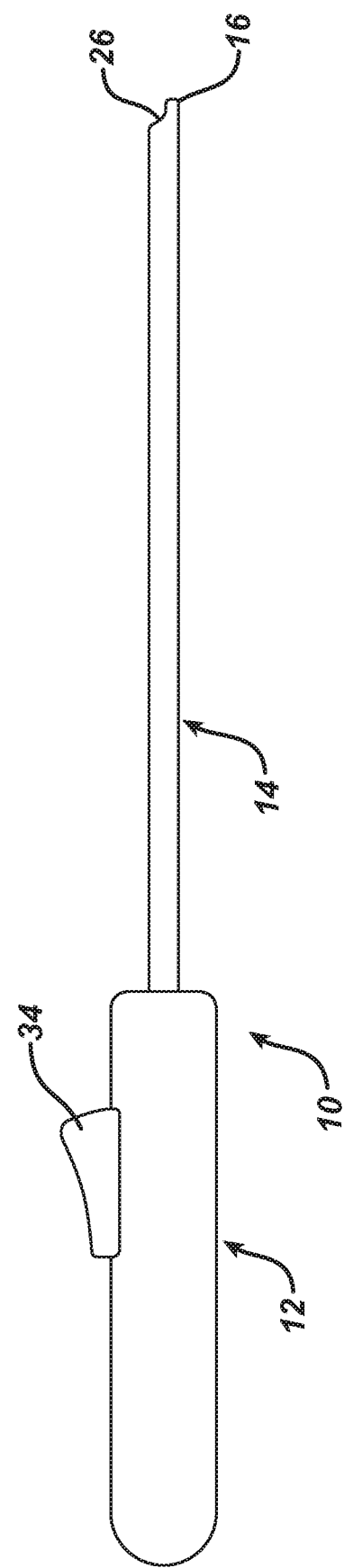
FIG. 1 is a side elevation view of an obturator according to the present invention.
Figure 2:
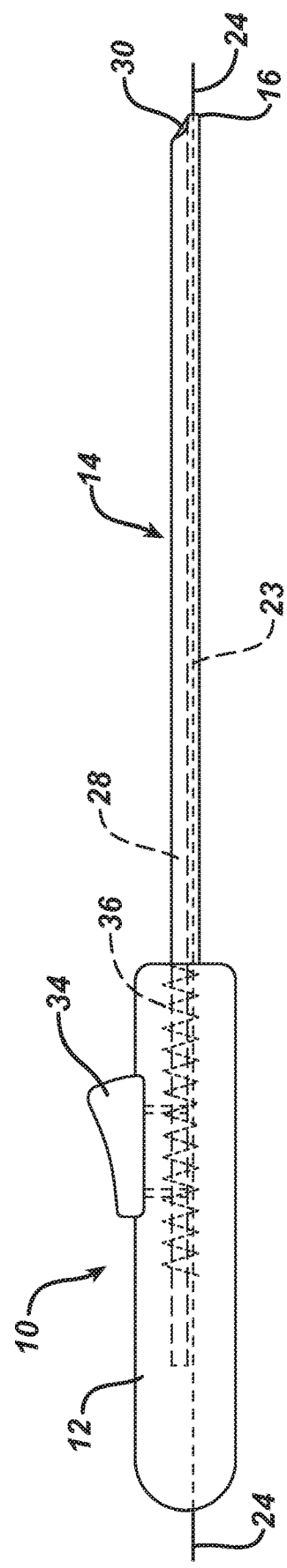
FIG. 2 is a further side elevation view of the obturator of FIG. 1.

FIGS. 1 and 2 illustrate an obturator 10 according to the present invention. It comprises a handle 12 having an elongated shaft 14 extending distally therefrom. The shaft 14 terminates in a distally projecting nub 16 offset from a central axis 18 of the shaft 12. The nub 16 extends from a proximal base 20 to a distal tip 22. The tip 22 is rounded to assist in penetration and to avoid tissue damage upon penetration. A lumen 24 passes through the obturator 10 from the handle 12, through the shaft 14 and exiting at the nub distal tip 22. It is sized to accommodate a guidewire 24.

Figure 3:
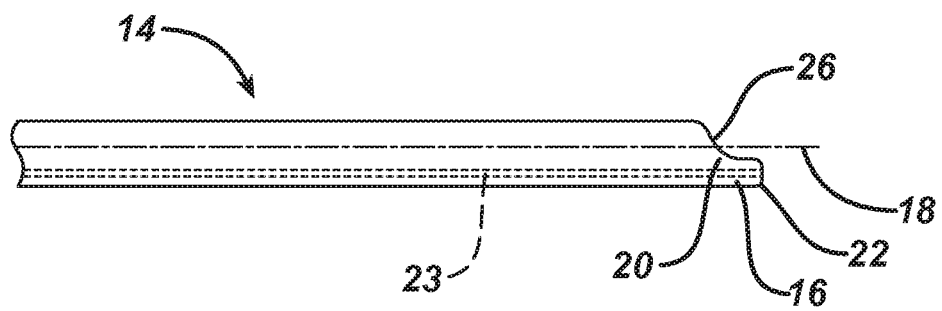
FIG. 3 is a side elevation view of a distal end of a shaft of the obturator of FIG. 1 with a blade in a retracted position.
Figure 4:
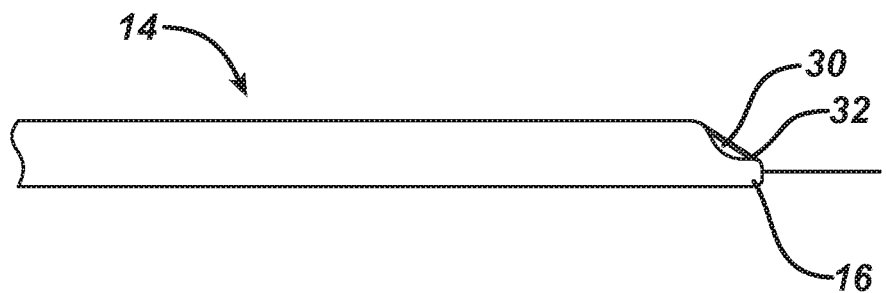
FIG. 4 is a side elevation view of the distal end of the shaft of the obturator of FIG. 1 with the blade in an extended position.

Turning also now to FIGS. 3 and 4, at the nub base 20 the shaft 14 extends to create an abutment 26. A blade member 28 operates within the shaft 14 and terminates with a distally facing blade 30. The blade 30 is preferably slanted having a distal end 32 adjacent the nub 16 and angling proximally therefrom. A button 34 on the handle 12 connects to the blade member 28 and allows a user to move the blade member 28 distally from a retracted position (FIG. 3) in which the blade 30 is retracted into the shaft 14 and not exposed to an extended position (FIG. 4) in which the blade 30 is exposed but does not extend beyond the nub distal end 22. Preferably, a spring 36 or other biasing means is provided to urge the blade member 28 into the retracted position. The blade 30 in its extended position preferably does not extend distally beyond the distal end 22 and preferably does not extend radially beyond the width of the shaft 14.

Turning also now to FIGS. 5A to 5F, use of the obturator 10 will now be explained with reference to a hip joint 40, although other uses are possible, such as for example a shoulder or a knee; applicability to any joint access procedure is anticipated. The hip joint 40 comprises a femoral head 42 on a femur 44 which is received within an acetabulum 46. A labrum 48 is a ring of cartilage which surrounds the acetabulum 46. A capsule 50 of fibrous tissue encloses the hip joint 40 extending from the acetabulum 46 to a neck 52 of the femur 44 between the femoral head 42 and the rest of the femur 44. The capsule 50 is comprised of very tough and fibrous tissue to protect the hip joint 46, but this toughness makes surgical access difficult. The obturator 10 allows a surgeon to access the hip joint 40 through the capsule 50 with greater ease than prior devices and methods.

Figure 5A:
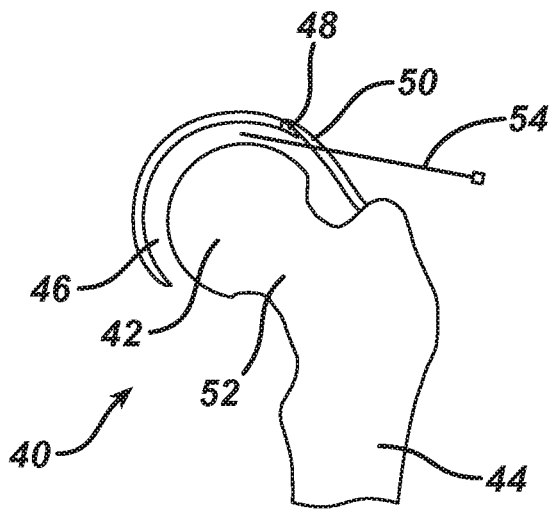
FIGS. 5A to 5F side elevation views in cross section of a hip joint being accessed by the obturator of FIG.
Figure 5B:
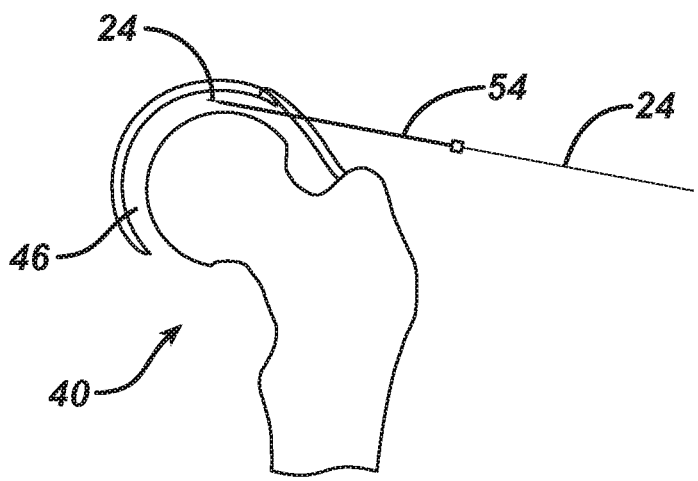
Figure 5C:
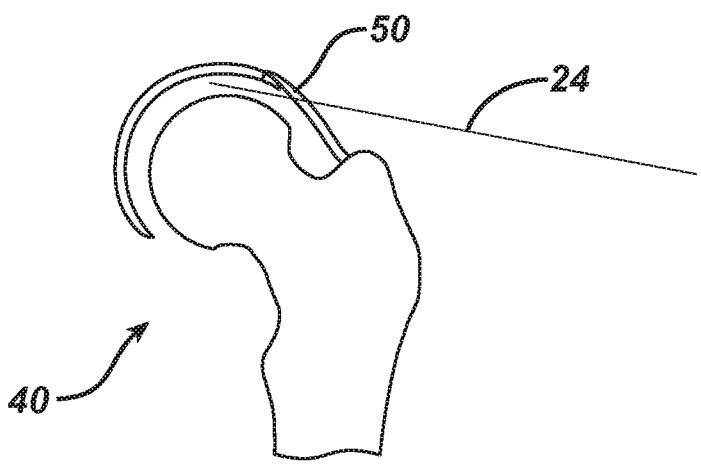
Figure 5D:
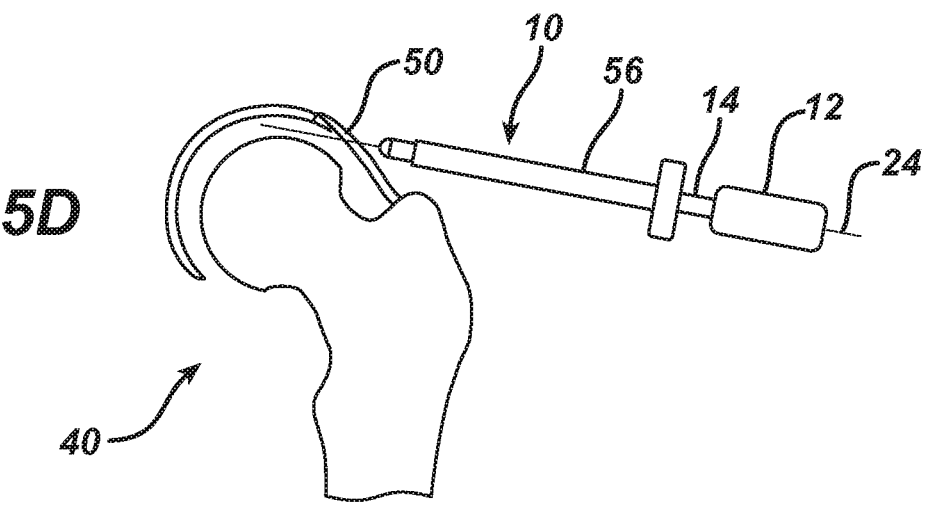
Figure 5E:
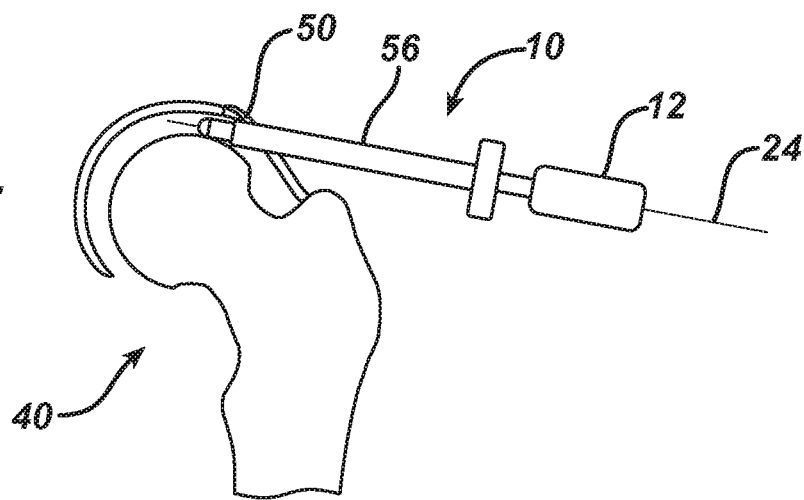
Figure 5F:
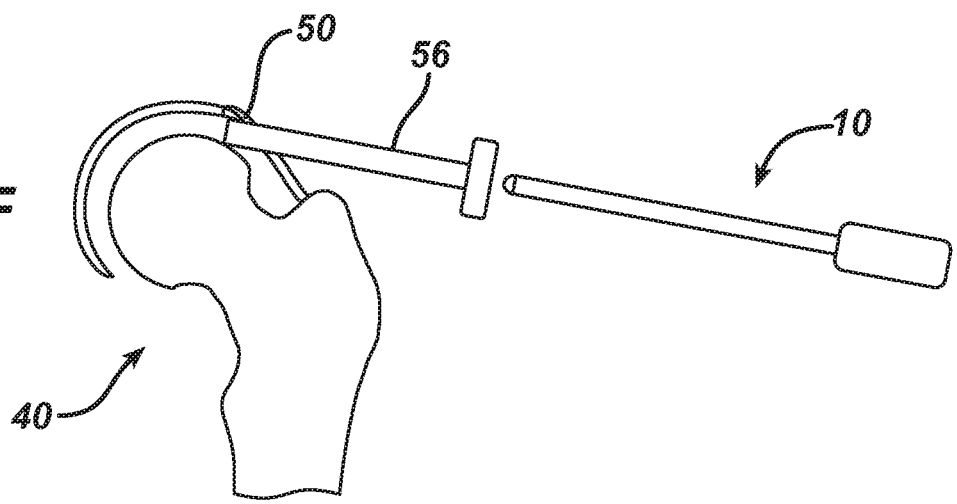

To access the hip joint 40, a cannulated spinal needle 54 is first introduced into the hip joint 40 in a preferred access orientation under the visualization of fluoroscopy. As is seen in FIG. 5A it enters a gap between the femoral head 42 and the labrum 48. The guidewire 24 is passed through the spinal needle 54 and placed into the acetabulum (FIG. 5B). The spinal needle 54 can then be removed (FIG. 5C). The obturator 10 is assembled to a scope sheath 56 or other access cannula type device and is passed down over the guidewire 24 until it reaches the capsule 50 (FIG. 5D). As used herein, the term "scope sheath" refers to a sheath employed with a surgical vision device such as an arthroscope, endoscope, laparoscope etc. The obturator 10 is advanced through the capsule 50 to create a hole 58 large enough to accommodate the scope sheath 56 (FIG. 5E). The details of how the obturator 10 penetrates the capsule 50 will be explained in reference to FIGS. 6A to 6F. Once the scope sheath 56 is received within the hip joint 40 through the capsule 50 the obturator 10 is removed therefrom (FIG. 5F) and a surgical procedure can then be performed in the hip joint 40, as for instance an arthroscopy camera (not illustrated) can be passed through the scope sheath 56 for visualization of the hip joint 40.

Figure 6A:
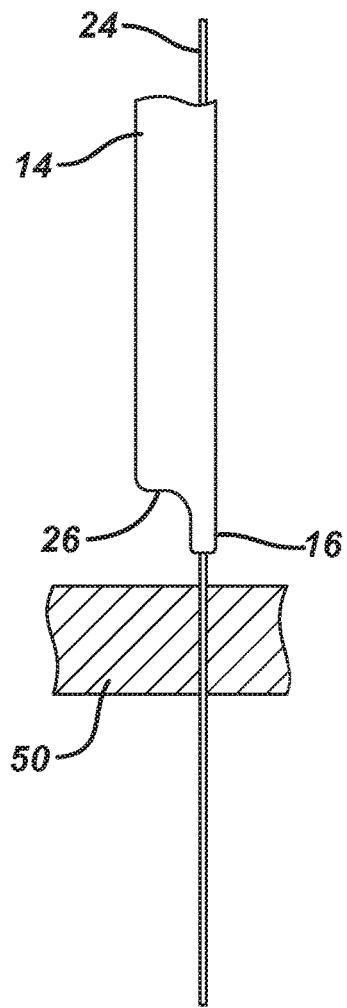
FIGS. 6A to 6F are side elevation views of capsule of the hip joint of FIGS. 5A to 5F being penetrated by the obturator of FIG. 1.
Figure 6B:
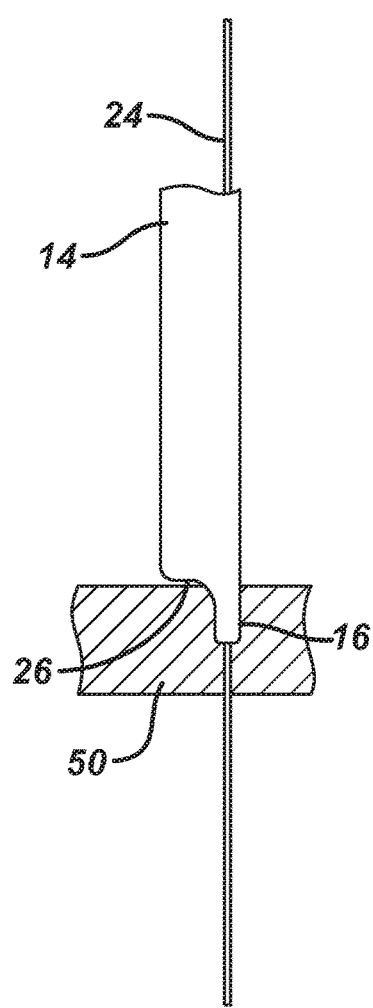
Figure 6C:
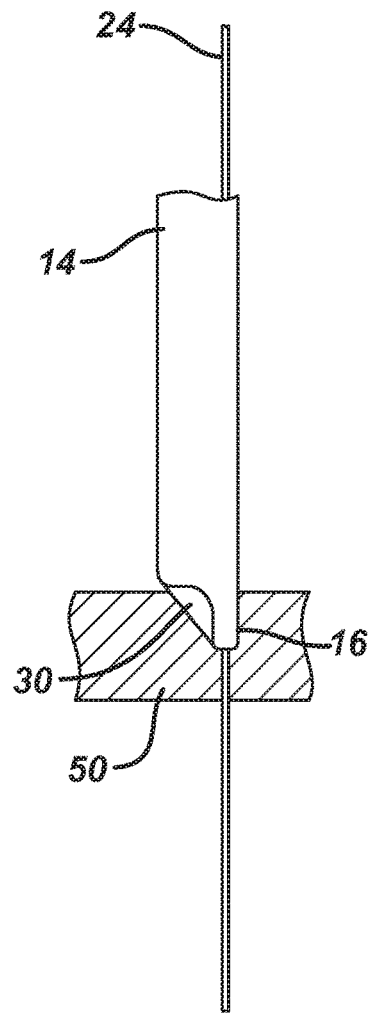
Figure 6D:
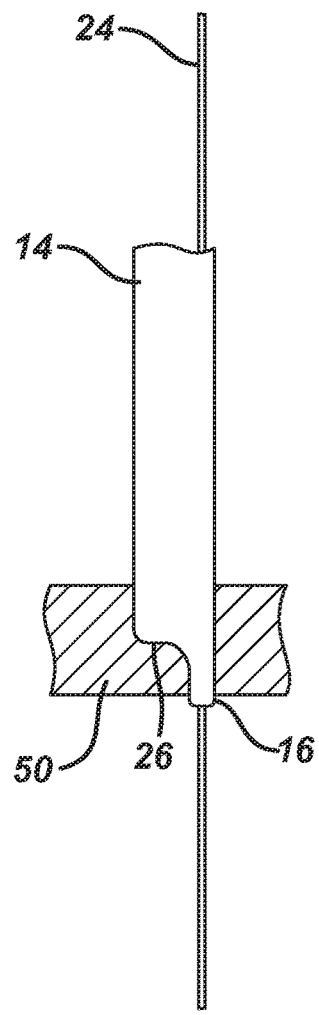
Figure 6E:
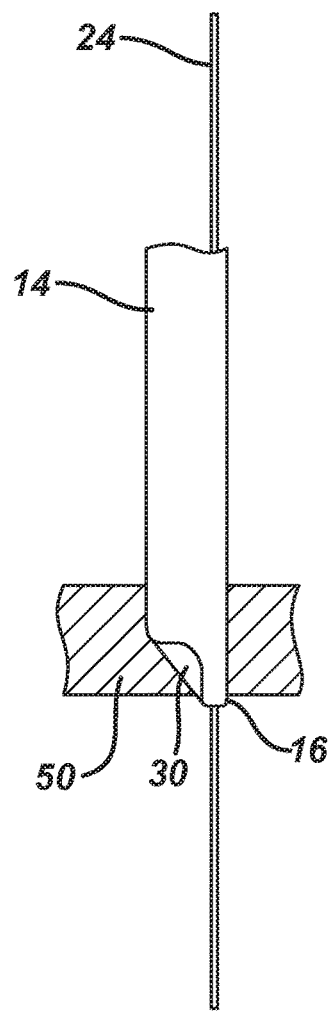
Figure 6F:
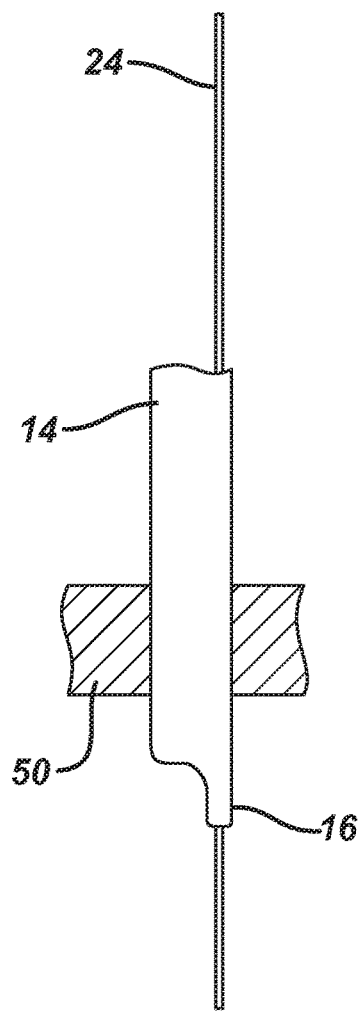

Turning now to FIGS. 6A to 6F the obturator 10 is shown without the scope sheath 56 for clarity. Its access through the capsule 50 begins with the nub 16 approaching the capsule 50 (FIG. 6A) and then being pressed therein with the blade 30 retracted until the abutment 26 abuts the capsule (FIG. 6B). The blade 30 is then extended to create a cut 60 in the capsule tissue 50 (FIG. 6C). Although a procedure could be performed comprising a single such cut 60, it is envisioned that a more controlled access can be provided with multiple smaller cuts 60. Thus, the blade 30 only partially penetrates the capsule 50 in FIG. 6C. The cut 60 provides access to allow the shaft 14 and abutment 26 to be pushed further into the capsule 50 with the blade 30 retracted (FIG. 6D) and the blade 30 is then again extended to expand the cut 60 further (FIG. 6E). After each such cut the blade 30 is retracted, and after several such cuts the shaft 14 has completely penetrated the capsule 50. Depending on the thickness of the capsule 50 and mode of use, typically about one to five cuts would be made, preferably three or fewer. By cutting and further by the abutment 26 access of the obturator 10 through the capsule 50 is controlled rather than explosive or sudden thereby greatly reducing the risk of it impacting and damaging tissue within the hip joint 40.

Cutting can be performed in other orientations. For instance, the shaft 14 can be rotated about the guidewire 24 with an additional cut or cuts being made opposite the cut 60 or in a star like pattern. The obturator 10 is shown with a single blade 30 offset from the central axis 18 but other configurations are envisioned such as a central hub with two or more blade edges extending radially therefrom.

Figure 7A:
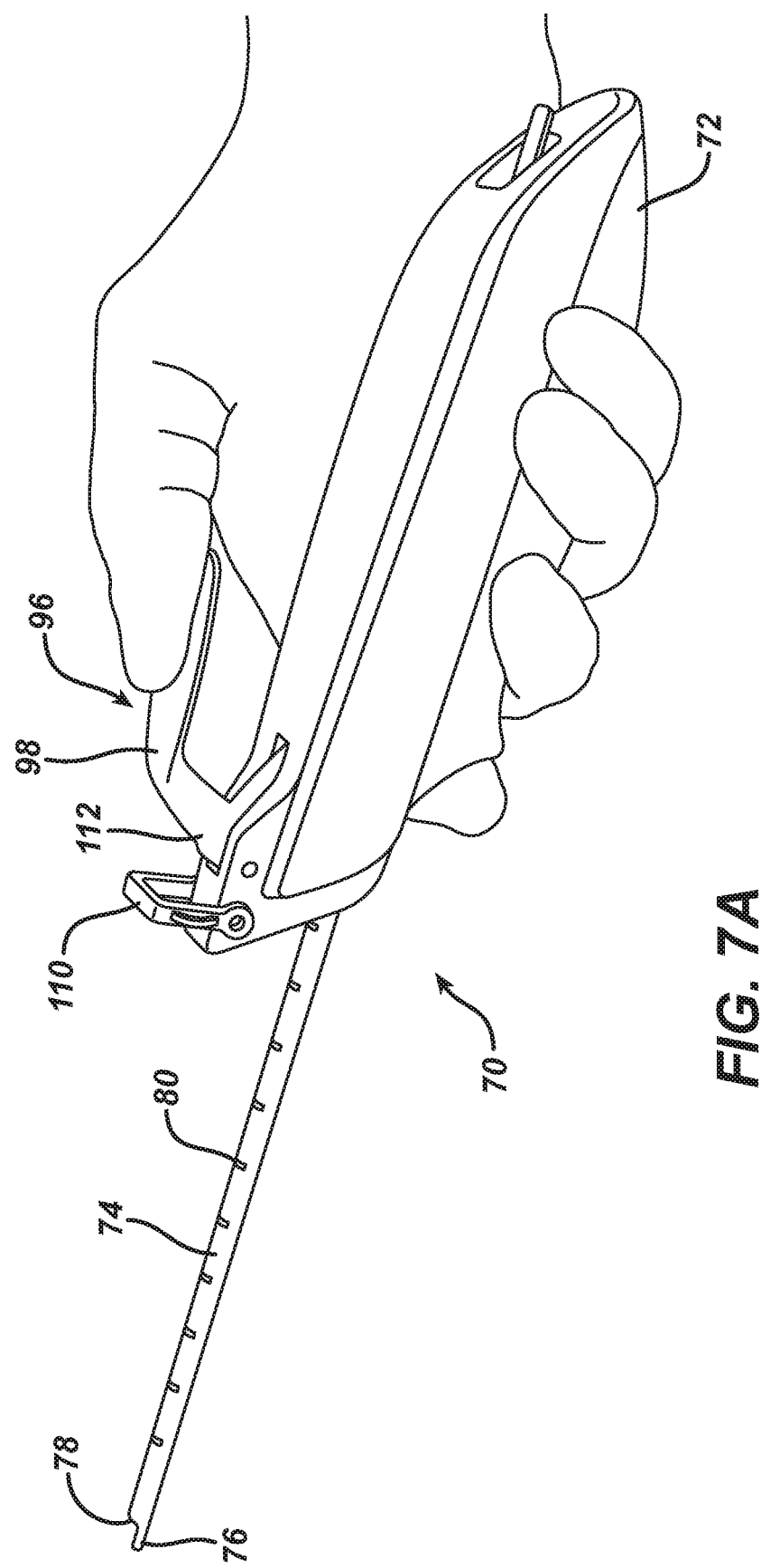
FIG. 7A is a perspective view of another embodiment of an obturator according to the present invention.
Figure 7B:
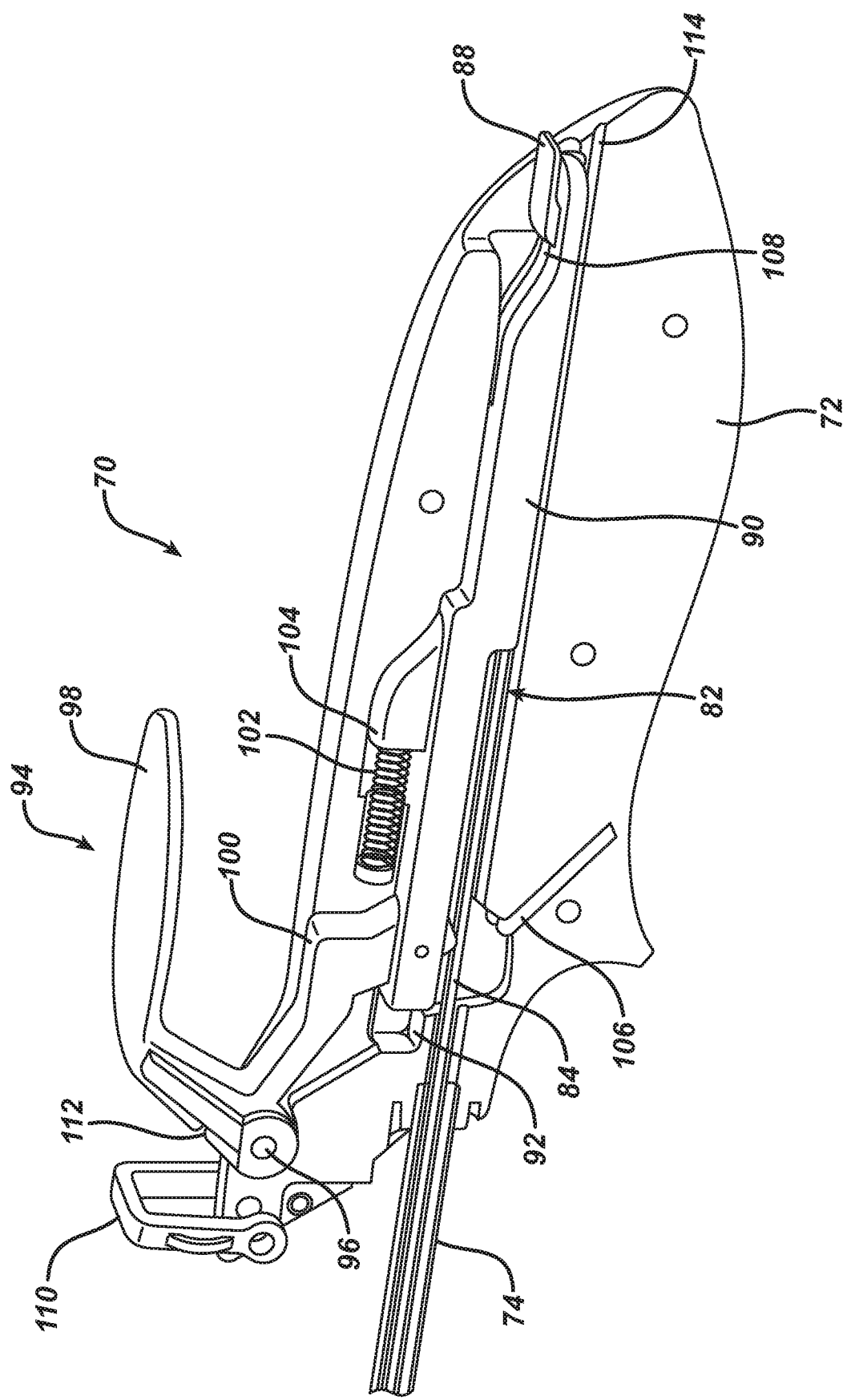
FIG. 7B is a perspective view in cross-section of the obturator of FIG. 7A.
Figure 8A:
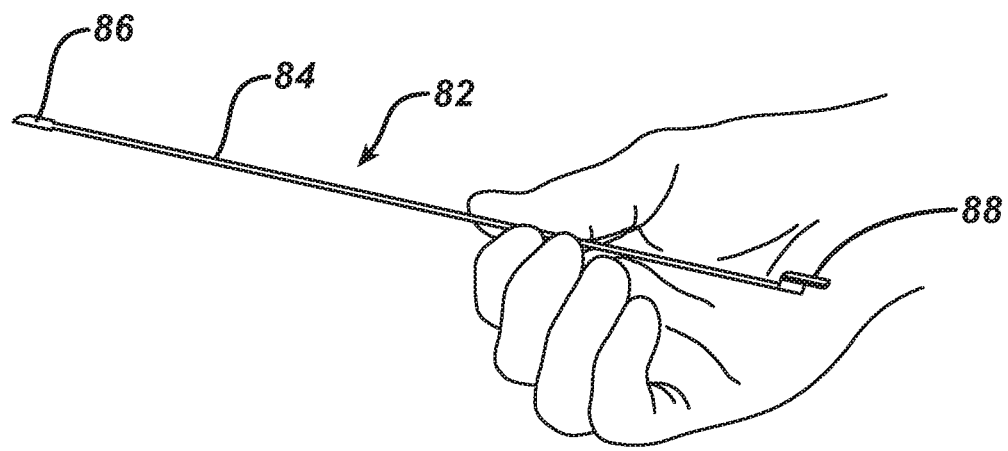
FIGS. 8A to 8D are perspective views of the obturator of FIG. 7A showing a blade member being loaded therein.
Figure 8B:
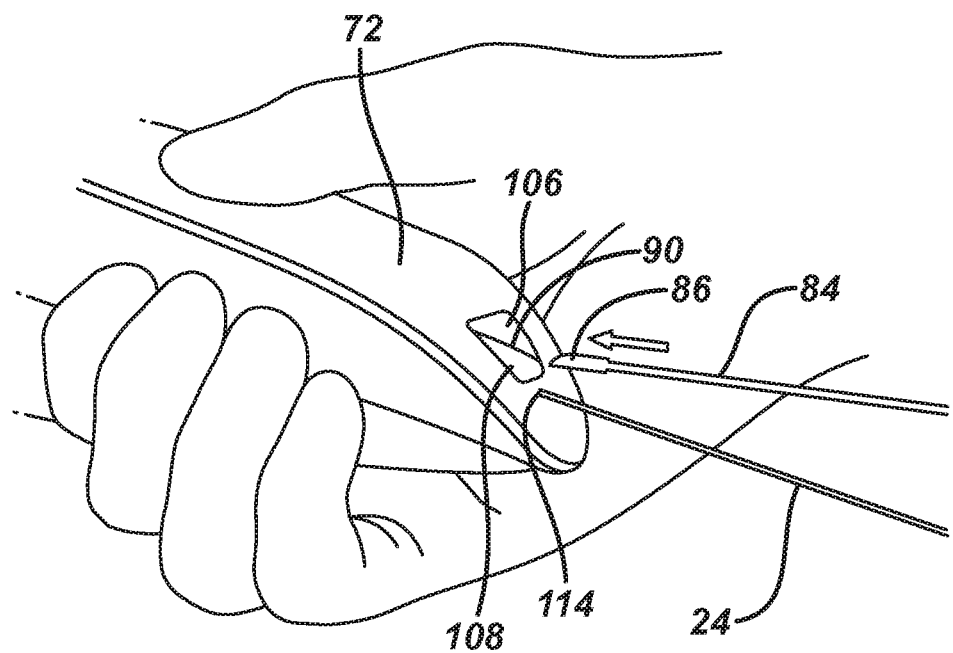
Figure 8C:
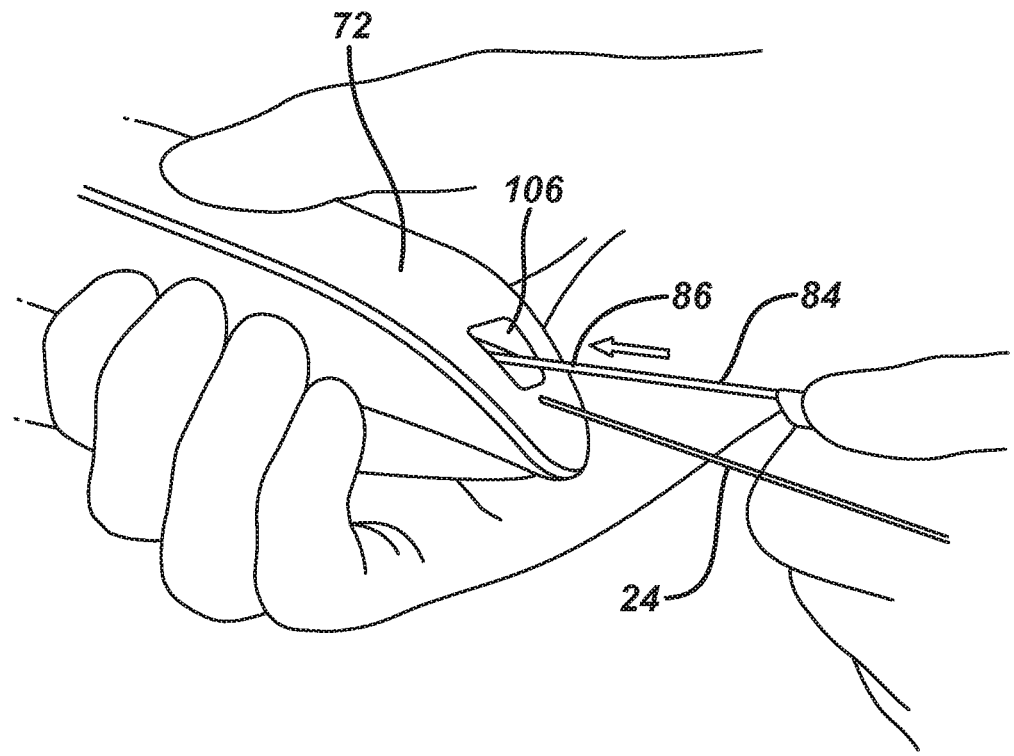
Figure 8D:
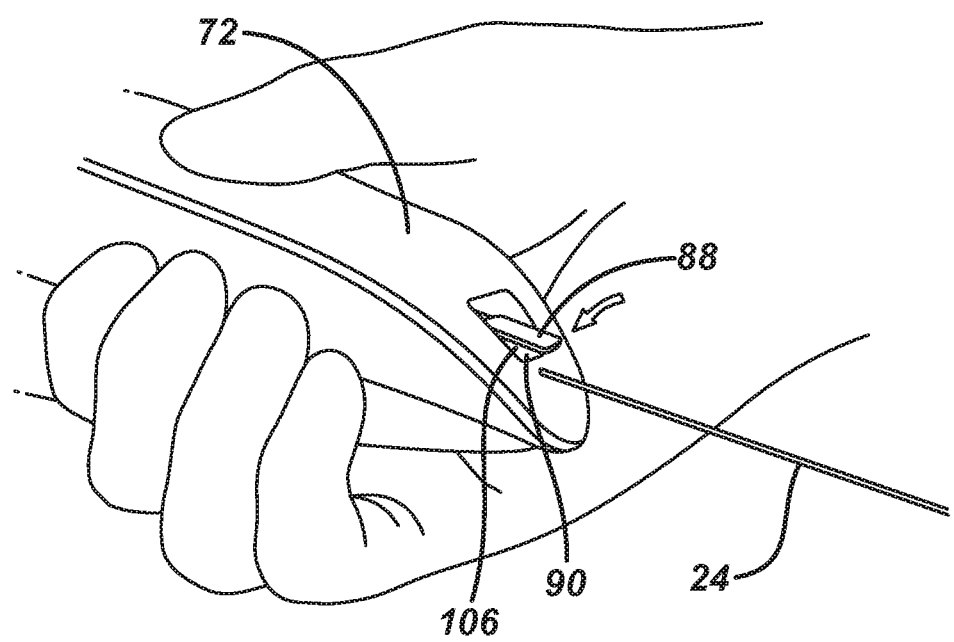

FIG. 7A illustrates a second embodiment of an obturator 70 according to the present invention. It comprises a handle 72 and a shaft 74 which terminates in a nub 76 defining an abutment 78 on the shaft 74. Depth markings 80 are provided on the shaft 74, preferably comprising annular grooves thereabout with printed depth indicia. Turning also to FIGS. 7B and 7C, a blade member 82 removably fits within the obturator 70 and comprises an elongated rod 84 which passes down the shaft 74 and terminates in a distal blade 86 (see FIGS. 8A and 8B). A proximal L-shaped grip 88 on the rod 84 fits within a sled 90 which travels proximally and distally within a chamber 92 in the handle 72. A lever 94 pivotably mounts about an axis 96 and carries a trigger 98 connected to an engagement leg 100 received within the sled 90 whereby rotation of the lever 94 induced by depressing the trigger 98 toward the handle 72 induces distal movement in the sled 90 thereby moving the blade member 82 distally. A spring 102 in the chamber 92 acts against an abutment 104 on the sled 90 to bias it proximally. An end of a flexible metal strip 106 in the handle projects into the chamber 92 to engage a protrusion 108 on the engagement leg 100 at the end of the travel of the trigger 98 to provide tactile feedback to a user. A latch 110 on the handle 72 engages a slot 112 on the trigger 98 to lock the lever 94 down with the blade 86 extended. A lumen 114 passes through the handle 72 and shaft 74 for receipt of the guidewire 24 (not shown in FIGS. 7A to 7C).

FIGS. 8A to 8D illustrate loading of the blade member 82 into the obturator 70 through a proximal opening 106 in the handle 72 until the grip 88 falls into a conforming recess 108 (see FIG. 7C) in the sled 90 which ensures that it will move proximally and distally in unison with the sled 90.

The obturator 70 is used in a similar fashion as previously described for the obturator 10. The handle 72 and shaft 74 may be reusable with the blade member 82 preferably being disposable. Accordingly, prior to use a new sterile blade member 82 is then loaded into the cleaned and sterilized handle 72 and shaft 74 assembly. To access the capsule 50, the nub 76 is advanced to the tissue and extension of the blade 84 is provided by squeezing the trigger 98 toward the handle 72.

After the capsule has been accessed the latch 110 can be engaged to lock the blade 86 in its exposed position to enable cutting therewith to perform a capsulotomy. In many procedures after a first visualization portal is established a second portal is established and these are often connected via a capsulotomy. By employing the blade 86 in the obturator 70, a separate blade need not be employed or exchanged down the portals. Alternatively, the blade member 82 is removed from the obturator 70 and is employed alone without the obturator to perform the capsulotomy. In another alternative, not shown, the blade may have a further extended position, distal of the nub 76, for enhanced cutting in performing a capsulotomy.

Figure 9:
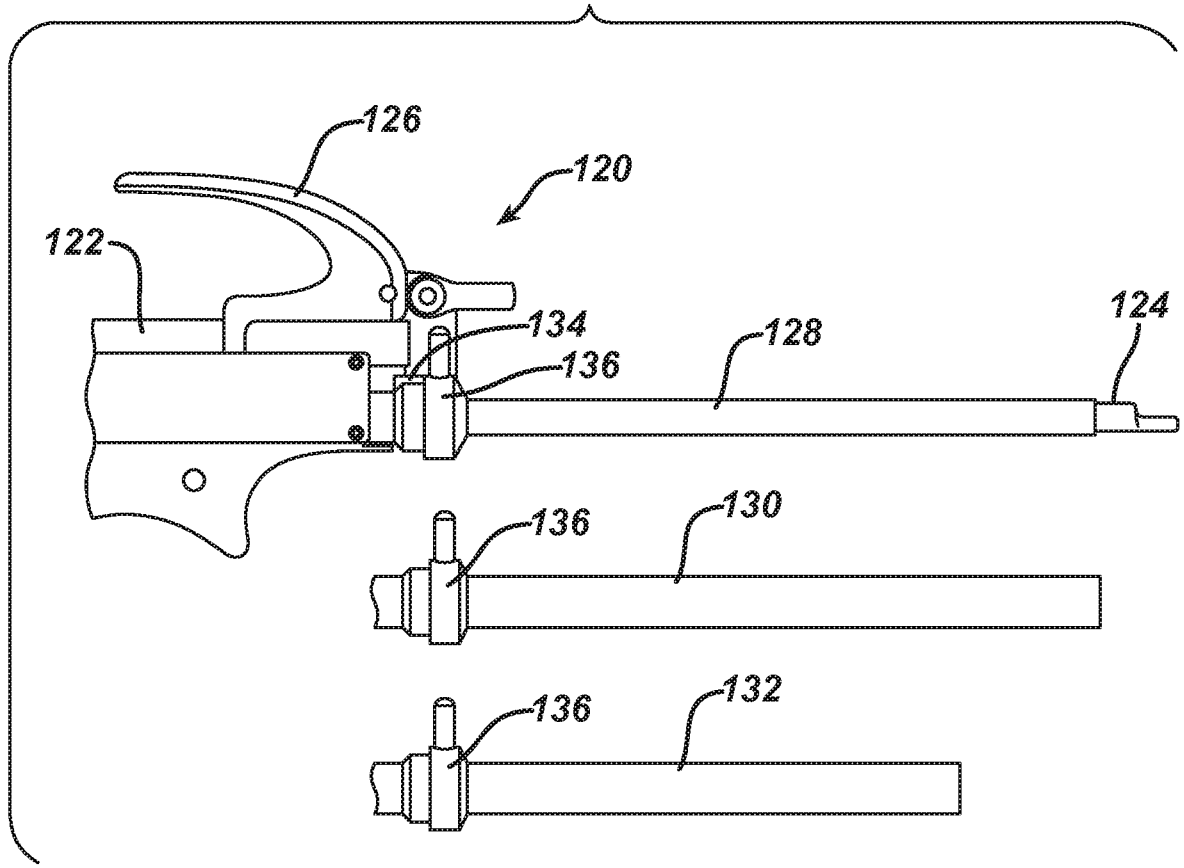
FIG. 9 is a side elevation view of a further embodiment of an obturator according to the present invention and a series of differently sized cannulas for use therewith.

FIG. 9 illustrates an obturator 120 according to the present invention having a handle 122, shaft 124 and trigger 126 similar to the obturator 70. Shown with the obturator 120 are three separate cannulas, or scope sheaths, 128, 130 and 132 of varying size, each of which is usable with the obturator 120. The top cannula 128 is shown fitted to the obturator 120. The shaft 124 fits closely within the cannula 128 and protrudes distally therefrom by only a short distance, ideally 3 mm or less from the distal end of the top cannula 128 to the abutment 26. If that distance were larger the cannula 128 may not enter the capsule with the obturator 120. The middle cannula 130 has a similar length to the cannula 120 but is or larger diameter such that the shaft 124 will not fit closely therein thereby creating a gap between the cannula 130 and the shaft 124 which will make passage through the capsule more challenging. The bottom cannula 132 has a larger diameter than the top cannula 128 and is also shorter. The handle 122 has a receiver 134 shaped to accommodate a proximal end fitting 136 of the cannulas 128, 130 and 132. It is contemplated that the handle 122 could be fitted with adapters (not shown) between the receiver 134 and fittings 136 to accommodate different types, shapes, and sizes of fittings 136 from various cannula manufacturers.

Figure 10:
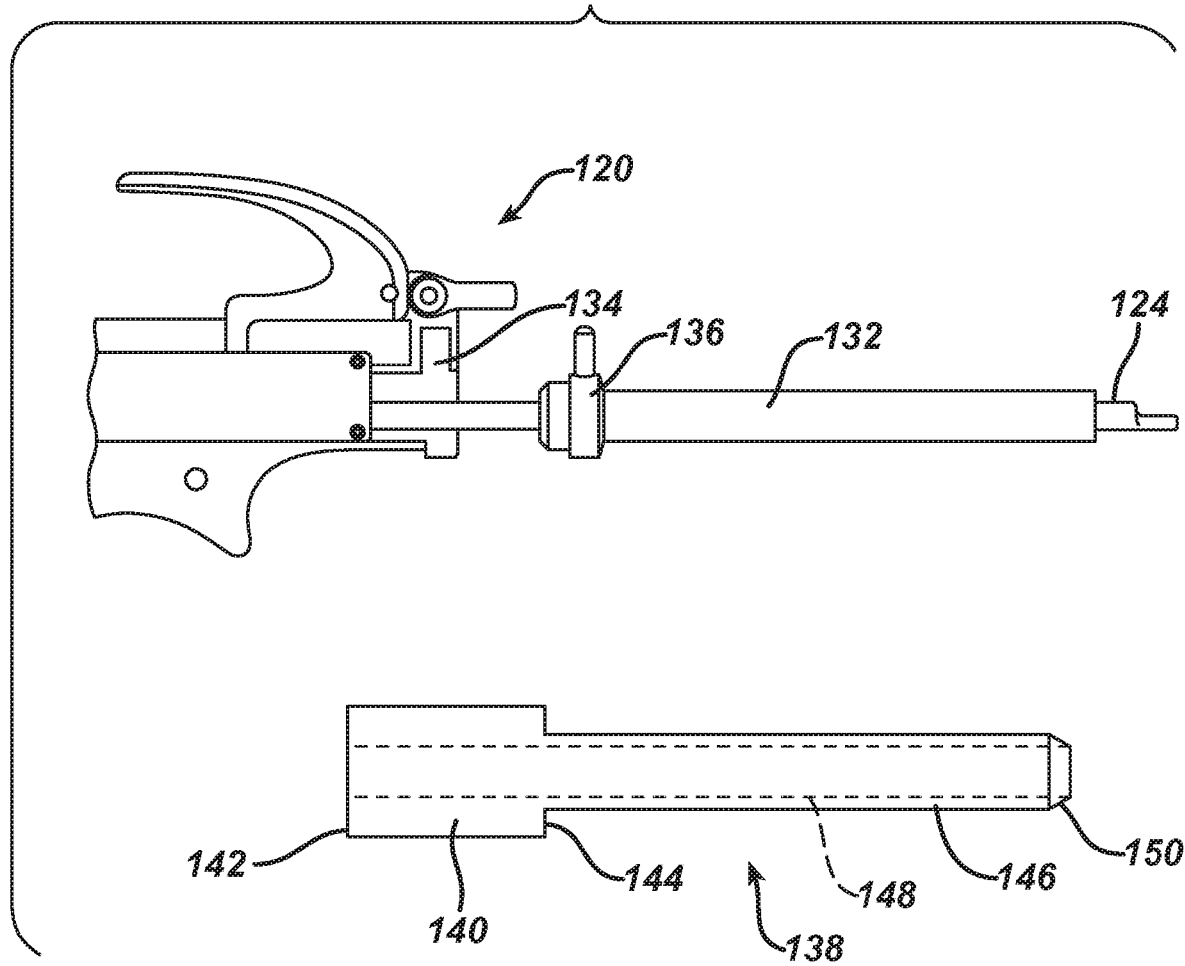
FIG. 10 is a side elevation view of the obturator and a cannula of FIG. 9 with a spacer to fit the cannula properly to the obturator.
Figure 11:
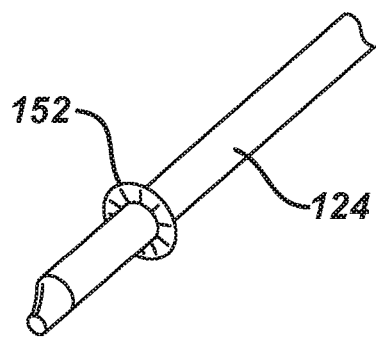
FIG. 11 is a perspective view of the obturator of FIG. 9 with a grommet-type spacer to fit a cannula properly to the obturator.

To accommodate shorter cannulas such as the bottom cannula 132, a spacer 138 (FIG. 10) can be provided. The spacer 138 comprises a proximal portion 140 which fits between the receiver 134 and fitting 136 and has a length adapted to place the cannula 128 on the shaft 124 with the desired length of the shaft 124 extending distally from the cannula 128. Its proximal end 142 can be shaped to fit within the receiver 134 and its distal end 144 shaped to receive the cannula fitting 136. Different spacers 138 can be provided with differently shaped proximal portion distal ends 144 to act also as an adapter and accommodate cannulas with different types, shapes, and sizes of fittings 136. An elongated tubular shim 146 extends distally from the proximal portion having a lumen 148 therethrough and a tapered distal end 150. It fits within the cannula 132 with the obturator shaft 124 received within its lumen 148. The tapered distal end 150 extends from the cannula 132 and provides a gentle transition from the diameter of the shaft 124 to the diameter of the cannula 132. The spacer 138 thus adapts both the length and the diameter of the cannula 132 to the obturator 120. For a cannula requiring only length adaptation the spacer 138 can omit the shim 146. For cannulas such as the middle cannula 130 of appropriate length but having a diameter larger than the shaft 124, the spacer 138 can omit the proximal portion 140 or have only a thin annular flange (not shown) adapted to fit between the receiver 134 and fitting 136. Alternatively, a grommet type spacer 152 (FIG. 11) can be fitted to the shaft 124 to provide a transition between it and the larger diameter of the cannula 130. It preferably fits with a friction fit to the shaft 124 with a higher force than its engagement with the cannula 132 whereby to allow it to be retracted through the cannula 132 without dislodgment from the shaft 124.

Figure 12A:
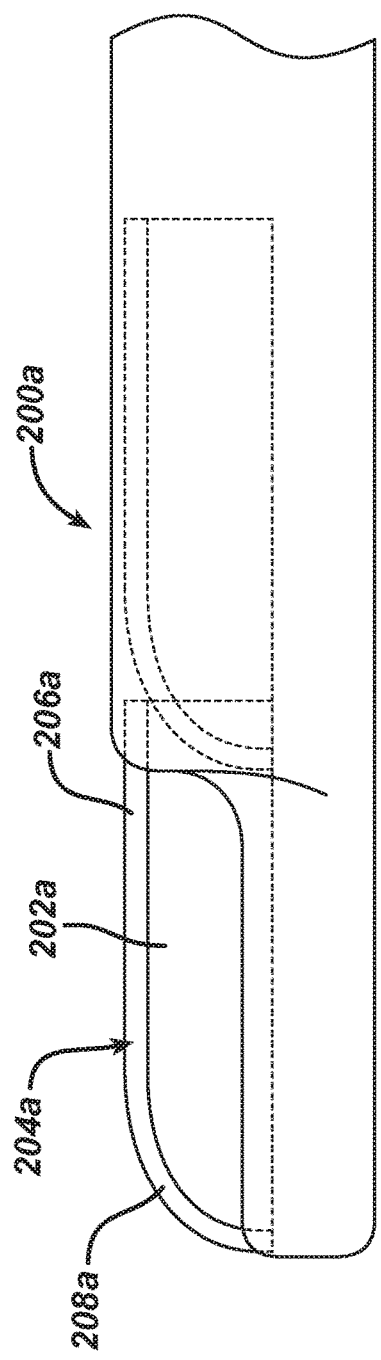
Figure 12B:
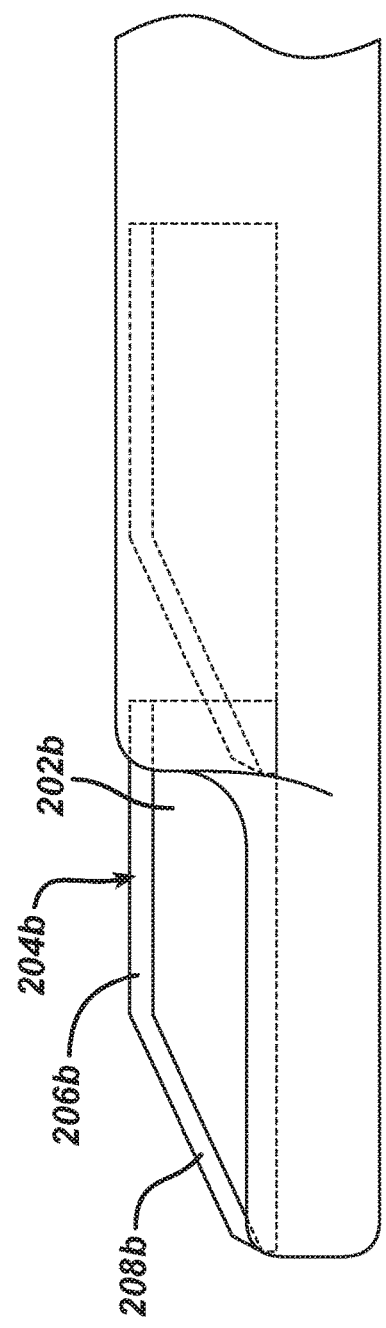
Figure 12C:
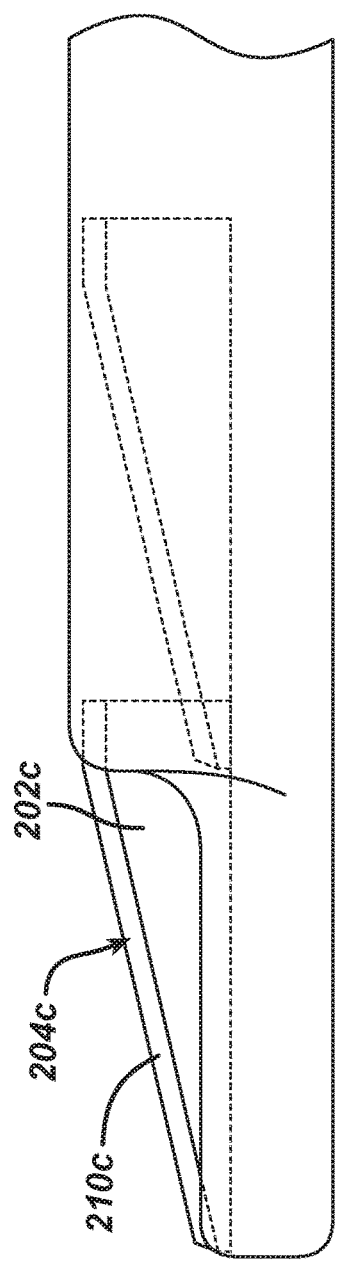

FIGS. 12A to 12F illustrate alternative blade designs. Like parts are indicated with like part numbers with the exception of the subscript. FIG. 12A illustrates an obturator 200a having a blade 202a with a cutting edge 204a extending along a straight side portion 206a and curved distal portion 208a. The blade 202a is shown in its extended position with its retracted position indicated in phantom. In FIG. 12B the blade 202b has its cutting edge 204b extending along a straight side portion 206b and an angled distal portion 208b. In FIG. 12C the blade 202c has its cutting edge 204c along an angled distally facing portion 210c. In FIG. 12D the blade 202d has its cutting edge 204d extending along a straight side portion 206d and straight distal portion 208d. In FIG. 12E the blade 202e has its cutting edge 204e extending along a straight side portion 206e and along a pointed distal portion 208e with relief 212e. In FIG. 12F the blade 202f has its cutting edge 204f extending along a straight side portion 206f and along a curved distal portion 208f with relief 212f. The invention is not limited to the blade shapes shown.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. For instance, it is contemplated that a blade member rather than being directly moved forward in ratio to movement of a trigger could instead be released to spring forward by actuating a trigger. The force would be provided by an internal spring or hammer which propels the blade member forward preferably in a predetermined manner such as with a predetermined force. The distal extent of the blade member movement would preferably be limited as in the embodiments disclosed. A mechanism similar to those employed in spring-loaded center punches could be employed so that the trigger handle would both load a spring and then release that stored energy such by overloading a separate spring-loaded ball-in-detent type retention on the blade member. Separate springs could be employed to return the trigger and blade member to their starting positions.

What is claimed is:

1. A hip arthroscopy obturator for penetrating a hip capsule, the obturator comprising:
  an axially elongated body having a distal end;
  a distal tip of the body at the body distal end, the distal tip having an outer diameter narrower than a body distal end diameter forming a distally facing abutment therebetween;
  a cannulation through the body to the distal end; and
  a retractable blade comprising a cutting edge and movable in a distal direction from a retracted position in which the cutting edge is disposed in the body and an extended position in which the cutting edge extends out of the body distally through the distally facing abutment, and wherein the cutting edge is slanted having a distal end adjacent the distal tip and angling proximally therefrom.

2. A hip arthroscopy obturator according to claim 1 wherein the blade is biased toward the retracted position.

3. A hip arthroscopy obturator according to claim 1 and further comprising a manually engageable actuator positioned proximal of the body distal end and connected to the blade whereby to allow a user to extend the blade to the extended position.

4. A hip arthroscopy obturator according to claim 1 wherein the body has a central longitudinal axis and the cannulation is offset laterally therefrom at the distal end.

5. A hip arthroscopy obturator according to claim 1 wherein the blade is movable from the retracted position to the extended position through the abutment.

6. A hip arthroscopy obturator according to claim 1 wherein when the blade is in the extended position the cutting edge does not extend distally beyond the distal tip nor laterally beyond the body distal end diameter.

7. A hip arthroscopy obturator according to claim 4 wherein the cannulation extend through the distal tip.

8. A hip arthroscopy obturator according to claim 1 and further comprising a guide wire extending through the cannulation.

9. A hip arthroscopy obturator according to claim 1 and further comprising a cannula having an axial lumen therethrough, the obturator being received within the lumen.

\* \* \* \* \*